United States Patent [19]

Nakazawa et al.

[11] Patent Number: 6,130,086
[45] Date of Patent: *Oct. 10, 2000

[54] COMPOSITION FOR AN IN VITRO FERTILIZATION MEDIUM

[75] Inventors: Teruki Nakazawa; Hiromasa Araki; Yuichiro Kishi; Sanji Shinoda; Moriyuki Yamada, all of Osaka; Kazutomo Ohashi, Ibaraki, all of Japan

[73] Assignee: Fuso Pharmaceutical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/029,063
[22] PCT Filed: Sep. 4, 1996
[86] PCT No.: PCT/JP96/02503
§ 371 Date: Mar. 2, 1998
§ 102(e) Date: Mar. 2, 1998
[87] PCT Pub. No.: WO97/08946
PCT Pub. Date: Mar. 13, 1997

[30] Foreign Application Priority Data

Sep. 4, 1995 [JP] Japan ................................. 7-226333

[51] Int. Cl.⁷ ............................. C12N 5/02; A61B 17/425
[52] U.S. Cl. ......................... 435/325; 435/408; 435/404; 435/346; 435/347; 435/366; 435/1.1; 435/2; 600/33; 600/34
[58] Field of Search .................... 435/408, 346, 435/347, 404, 325, 366, 1.12, 2; 600/33, 34

[56] References Cited

PUBLICATIONS

ATCC Catalogue of Cell Lines & Hybridomas, 6th Ed. pp. 352–353, 1988.
1995:163945 Biosis (Abstract).
Chemical Abstracts 91(1):268x, 1979.
Chemical Abstracts 101(13):108020, 1984.
Liu et al, Human Reproduction 10(11):2985–2991,1995.
Gutmann et al. J. Clin. Endocrin. Metab. 76(5):1314–1318 (1993).
Li et al, Biol. Reprod. 48:33–37, 1993.
Dumoulin et al, J. Reprod. Fert. 94:373–380, 1992.
Reed et al, Theriogenology 37(1):95–109, 1992.
Van Winkle et al, Biol. Reprod. 52:96–104, 1995.

*Primary Examiner*—Francisco Prats

[57] ABSTRACT

The present invention aims to provide a medium composition for in vitro fertilization, in particular, a composition usable in the culture of ova or early embryos which are fertilized eggs, the preparation or culture of sperm, and the pre-treatment of ova or sperm.

The composition comprises, as its essential components, L-phenylalanine, L-tryptophan, L-lysine, L-threonine, L-valine, L-methionine, L-isoleucine, L-leucine, L-proline, glycine, L-alanine, L-tyrosine, L-histidine, L-arginine, L-taurine, L-aspartic acid, L-serine, L-asparagine, L-glutamic acid, L-glutamine and L-cystine, provided that at least a part of the L-cystine may be replaced by L-cysteine.

2 Claims, No Drawings

COMPOSITION FOR AN IN VITRO FERTILIZATION MEDIUM

TECHNICAL FIELD

The present invention relates to a culture medium composition for in vitro fertilization, in particular, applied to the culture of ova or early embryos which are fertilized ova or to the pretreatment of ova or sperm. In particular, the composition of the medium according to the present invention is effective for the stimulation of the growth and qualitative stabilization of early embryos and is suitable for the culture of early embryos.

BACKGROUND ART

The so-called in vitro fertilization and embryo transfer comprises fertilizing ova and sperm in vitro and then transplanting the developed embryos into a female body. Since the world's first case of a human birth was reported in England in 1978 by Edwards et.al., and along with recent progress in the developmental technology, this treatment has been rapidly and widely used in Japan, and it is now an indispensable treatment for sterility.

However, there are still few cases that lead to pregnancy by the method, and it can not be said that the method is completely established. This may be because of the lower fertility in sterile patients due to male factor, but the lower implantation rate of ova to be transplanted seems to be main cause ((Mori,Munehide et.al., Nippon sankahujin kagakukai zashi, v.45, p.397(1993); Cohen,J. et al., VIIIth World Congress on in vitro Fertilization and Alternate Assisted Reproduction Kyoto, Sep., 12–15(1993), World Collaborative Report(1991)).

In addition to the technical factors, a lowering in the quality of embryos during culture seems to be responsible for such lower implantation rates (Inoue, Masahito, Rinsho fujinka sanka, v.48, p.148(1994)). That is to say, ova of mammalia do not have substances that correspond to the albumin in the eggs of reptiles and birds, and therefore, the amounts of nutrient reserved in the mammalian ova are naturally low. Thus, in the early embryos of in vitro fertilization, nutrient factors must be taken up through the zona pellucida from the culture medium. However, chemically defined media such as Ham's F-10 medium, MEM (Minimum Essential Medium), Dulbecco's MEM and the like, which have been conventionally utilized in in vitro fertilization, were not originally composed for the purpose of in vitro fertilization, but they are the media used conventionally in tissue culture or their modified media, therefore it cannot be said that they are the optimal media for the early embryos regarding the nutrient composition.

Recently, HTF medium (Human Tubal Fluid Medium) has been developed as nutriologically suitable medium for human in vitro fertilization, with a composition approximating to the electrolyte of human oviduct fluid (Quinn,P. J. et al., Fertility and Sterility, v.44, p.493(1982)). The medium is commercially available and replaces Ham's F-10 medium that was used predominantly so far. However, because the HTF medium only contains electrolytes as the main components and glucose as an energy source, the HTF medium shows no improvement over the Ham's F-10 medium containing amino acids, as regards the nutrient composition. In fact, despite the use of this medium, the implantation rate can not be enhanced though any substantial improvement in the problem of the lowering in quality of embryos.

In order to make up for this disadvantage, a method has been utilized in which the embryos are fed by adding the female serum which has been inactivated by heat treatment to the medium. The serum contains growth factors and the like, in addition to proteins, carbohydrates, lipids, vitamins and minerals as five nutrients which are essential factors in animal cell culture. For reason, the serum is added during embryo culture.

However, it has been reported that such serum is not always needed in the in vitro fertilization-embryo transfer process (Menezo,Y. et al., Fertility and Sterility v.42, p.750 (1984)) and that on the contrary the growth of embryos may be suppressed by the addition of serum (Mehita, et al.Biology of Reproduction v.43, p.600 (1990)). Also, the serum itself is troublesome to collect and there is a danger of contamination by viruses etc. Therefore, the serum is not suitable as an additive for the medium of an in vitro fertilized ova.

At present, the substance which is mostly noted as the embryo growth-suppressing factor is oxygen free radical. This is based on the idea that the growth of embryos is suppressed by oxidative stress due to more opportunities of direct contact with oxygen in vitro, compared with in vivo (Whitten,W., Advanced in the Biosciences v.6, p.129 (1971); Quinn, P. J. et al., Journal of Experimental Zoology, v.206, p.73 (1978)). On the basis of this idea, it has been tried to prevent such oxidative stress for enhancing the growth of embryos by adding superoxide dismutase (SOD), edetic acid (EDTA) and the like to a medium (Abramczuk, J. et al., Developmental Biology, v.61, p.378 (1977); Nonozaki, T. et al., Journal of Assisted Reproduction and Genetics, v.9, p.274 (1992)).

It has also been reported that co-cultures using the epithelial cells of the oviduct whose effective components are unknown are effective for the growth of embryos (Xu, K. P. et al., Journal of Reproduction and Fertility, v.94, p.33 (1992)) and that a growth factor such as an insulin-like growth factors directly stimulates the growth of embryos (Matui, Motozumi et al., Honyudoubutu ranshi gakkaishi, v.11, p.132 (19949).

However, an analysis result has also been reported in which such a co-culture is, at most, effective for the detoxification of a medium and there is no evidence available of feeding to the embryos (Bavister, B. D., Human Reproduction, v.7, p.1339 (1992)). In any event, any conventional media for in vitro fertilization and any methods for adding additives to them as described above, including the addition of superoxide dismutase, EDTA and the like, merely partially prevent the cessation of the growth in vitro. Furthermore, there are very inconvenient to handle because, in actual culture of embryos, the optimal media corresponding to the embryo's growth stages must be suitably selected and exchanged at every stages.

Accordingly, in this technical field, the development of a chemically defined medium which contains a nutrient composition suitable for treatment/pretreatment of sperm or ovum as well as for growing of early embryo in the in vitro fertilization-embryo transfer process, which can be applied to all the growth stages of early embryo, and which is safe and leads to no danger of possible contamination of toxic substances such as viruses has been demanded.

SUMMARY OF INVENTION

The present inventors have carried out extensive researches regarding the above demands. As a result of such research, we have focused attention on amino acid compositions utilized in the protein synthesis, and found that when a medium containing amino acids corresponding to those contained in the fluid of the ovarian follicle is used as a medium composition for in vitro fertilization, the growth of early embryos in an in vitro fertilization-embryo transfer is greatly enhanced. The present invention was thus achieved on the basis of such finding.

The present invention provides a medium composition for in vitro fertilization comprising, as its essential components, twenty-one amino acids contained in the ovarian follicular fluid. These twenty-one amino acids are determined by collecting ovarian follicular fluid from 21 patients to be in vitro fertilized after administrating an ovulation inducer, and analyzing the resulted fluid by conventional methods (see the following Table 1). In particular, the amino acids include L-phenylalanine, L-tryptophan, L-lysine, L-threonine, L-valine, L-methionine, L-isoleucine, L-leucine, L-proline, glycine, L-alanine, L-tyrosine, L-histidine, L-arginine, L-taurine, L-aspartic acid, L-serine, L-asparagine, L-glutamic acid, L-glutamine and L-cystine.

TABLE 1

List of Composition of Amino acid (mg/l)

| amino acid | follicular fluid (found amount) | | | serum (found amount) |
|---|---|---|---|---|
| | Minimum (Min group) | Mean (F group) | Maximum (Max group) | Mean (S group) |
| Phe: phenylalanine | 4.63 | 6.89 | 8.76 | 9.27 |
| Trp: tryptophan | 3.27 | 6.74 | 9.39 | 7.87 |
| Lys: lysine[a] | 14.61 | 24.42 | 34.89 | 30.04 |
| Thr: threonine | 10.24 | 14.77 | 21.68 | 16.93 |
| Val: valine | 7.97 | 16.56 | 22.84 | 21.86 |
| Met: methionine | 1.04 | 2.13 | 3.28 | 3.13 |
| Ile: isoleucine | 2.36 | 4.48 | 6.17 | 7.63 |
| Leu: leucine | 3.67 | 7.88 | 10.49 | 14.15 |
| Pro: proline | 7.71 | 11.68 | 15.77 | 12.55 |
| Gly: glycine | 7.43 | 11.59 | 21.55 | 13.66 |
| Ala: alanine | 19.42 | 26.62 | 48.29 | 28.29 |
| Cys: cystein[b] | — | — | — | — |
| Tyr: tyrosine | 3.99 | 7.70 | 12.50 | 8.69 |
| His: histidine[b] | 13.42 | 16.25 | 22.01 | 18.89 |

TABLE 1-continued

List of Composition of Amino acid (mg/l)

| amino acid | follicular fluid (found amount) | | | serum (found amount) |
|---|---|---|---|---|
| | Minimum (Min group) | Mean (F group) | Maximum (Max group) | Mean (S group) |
| Arg: arginine[a] | 7.80 | 11.22 | 22.12 | 15.93 |
| Tau: taurine | 1.75 | 3.92 | 12.26 | 15.48 |
| Asp: aspartic acid | 0.53 | 0.86 | 1.46 | 2.87 |
| Ser: serine | 5.15 | 7.76 | 12.19 | 13.31 |
| Asn: asparagine[c] | 4.05 | 9.73 | 24.92 | 11.60 |
| Glu: glutamic acid | 9.71 | 13.62 | 20.89 | 13.20 |
| Gln: glutamine | 14.76 | 26.13 | 35.95 | 29.29 |
| Cys—Cys: cystine | 0.24 | 1.35 | 4.09 | 1.44 |
| Orn: ornithine | — | — | — | — |
| Amino butyric acid | — | — | — | — |
| Hydroxy proline | — | — | — | — |

[a]HCl
[b]HCl.H$_2$O
[c]H$_2$O

In Table 1, the F group shows the mean values of actual measurements on the follicular fluid from twenty-one patients, the F-Max and F-Min groups are, respectively, the maximum and minimum values of actual measurements from twenty-one patients. Further, the S group shows the mean values of actual measurements on the serum from twenty-one patients.

So far, no medium which contains all of these twenty-one amino acids and only these amino acids has been used in this technical field. For example, as shown in the following Tables 2 and 3, none of the representative seventeen chemically defined media corresponding to the prior art against the present invention contains the taurine found in the follicular fluid except for the NCTC 135 medium. On the other hand, the NCTC 135 medium contains hydroxy proline which is not found in the follicular fluid. Thus, none of the medium compositions in these prior arts disclose and suggest the new amino acid composition according to the present invention.

TABLE 2

Amino acid composition of the medium of the prior art (concentration: mg/l), part 1

| | Chemically defined medium | | | | | | | | |
|---|---|---|---|---|---|---|---|---|---|
| Amino acid | 199 | BME | CMRL 1066 | MEM | α-MEM | Dulbecco's MEM | McCoy's 5a | RPMI 1640 | Waymouth's MB 752/1 |
| Phe: phenylalanine | 25.0 | 16.5 | 25.0 | 33.0 | 33.0 | 66.0 | 16.5 | 15.0 | 50.0 |
| Trp: tryptophan | 10.0 | 4.0 | 10.0 | 10.2 | 10.2 | 16.2 | 3.1 | 5.0 | 40.0 |
| Lys: lysine | 70.0 | 36.5 | 70.0 | 73.1 | 73.1 | 146.2 | 36.5 | 40.0 | 240.0 |

TABLE 2-continued

Amino acid composition of the medium of the prior art (concentration: mg/l), part 1

| | Chemically defined medium | | | | | | | | |
|---|---|---|---|---|---|---|---|---|---|
| Amino acid | 199 | BME | CMRL 1066 | MEM | α-MEM | Dulbecco's MEM | McCoy's 5a | RPMI 1640 | Waymouth's MB 752/1 |
| Thr: threonine | 30.0 | 23.8 | 30.0 | 47.6 | 47.6 | 95.2 | 17.9 | 20.0 | 75.0 |
| Val: valine | 25.0 | 23.4 | 25.0 | 46.8 | 46.9 | 93.6 | 17.6 | 20.0 | 65.0 |
| Met: methionine | 15.0 | 7.5 | 15.0 | 14.9 | 14.9 | 30.0 | 14.9 | 15.0 | 50.0 |
| Ile: isoleucine | 20.0 | 26.2 | 20.0 | 52.5 | 52.5 | 104.8 | 39.4 | 50.0 | 25.0 |
| Leu: leucine | 60.0 | 26.2 | 60.0 | 52.4 | 52.5 | 104.8 | 39.4 | 50.0 | 50.0 |
| Pro: proline | 40.0 | — | 40.0 | — | 40.0 | — | 17.3 | 20.0 | 50.0 |
| Gly: glycine | 50.0 | 10.5 | 50.0 | — | 50.0 | 30.0 | 7.5 | 10.0 | 50.0 |
| Ala: alanine | 25.0 | — | 25.0 | 126.4 | 25.0 | — | 13.4 | 200.0 | — |
| Cys: cystein | 0.10 | — | 260.0 | — | 100.0 | — | 35.1 | — | 90.0 |
| Tyr: tyrosine | 40.0 | 18.1 | 40.0 | 36.2 | 36.2 | 72.0 | 18.1 | 20.0 | 40.0 |
| His: histidine | 21.9 | — | 20.0 | 41.9 | 41.9 | 42.0 | 21.0 | 15.0 | 164.1 |
| Arg: arginine | 70.0 | 21.1 | 70.0 | — | 126.4 | 84.0 | 42.1 | 56.8 | 75.0 |
| Tau: taurine | — | — | — | — | — | — | — | — | — |
| Asp: aspartic acid | 30.0 | — | 30.0 | — | 30.0 | — | 20.0 | 20.0 | 60.0 |
| Ser: serine | 25.0 | — | 25.0 | — | 25.0 | 95.2 | 26.3 | 30.0 | — |
| Asn: asparagine | — | — | — | — | 50.0 | — | 45.0 | — | — |
| Glu: glutamic acid | 66.8 | — | 75.0 | — | 75.0 | — | 22.1 | 20.0 | 150.0 |
| Gln: glutamine | 100.0 | 292.0 | 100.0 | 292.0 | 292.0 | 584.0 | 219.2 | 300.0 | 350.0 |
| Cys-Cys: cystine | 20.0 | 12.0 | 20.0 | 24.0 | 24.0 | 48.0 | — | 50.0 | 15.0 |
| Orn: ornithine | — | — | — | — | — | — | — | — | — |
| Amino butyric acid | — | — | — | — | — | — | — | — | — |
| Hydroxy proline | 10.0 | — | 10.0 | — | — | — | 19.7 | 20.0 | — |

TABLE 3

Amino acid composition of the medium of the prior art (concentration: mg/l), part 2

| | Chemically defined medium | | | | | | | |
|---|---|---|---|---|---|---|---|---|
| Amino acid | Trowell's T8 | Ham's F-10 | Ham's F-12 | Leibovitz's L-15 | NCTC 135 | Williams' E | Kane and Foote | MCDB 104 |
| Phe: phenylalanine | 33.0 | 5.0 | 5.0 | 125.0 | 16.5 | 25.0 | 5.0 | 4.956 |
| Trp: tryptophan | 4.0 | 0.6 | 2.0 | 20.0 | 17.5 | 10.0 | 0.6 | 2.042 |
| Lys: lysine | 36.0 | 29.3 | 36.5 | 93.7 | 38.4 | 87.5 | 29.3 | 36.54 |
| Thr: threonine | 48.0 | 3.6 | 11.9 | 300.0 | 18.9 | 40.0 | 3.6 | 11.91 |
| Val: valine | 23.0 | 3.5 | 11.7 | 100.0 | 25.0 | 50.0 | 3.5 | 11.72 |
| Met: methionine | 7.5 | 4.5 | 4.5 | 75.0 | 4.4 | 15.0 | 4.5 | 4.476 |
| Ile: isoleucine | 26.0 | 2.6 | 3.9 | 125.0 | 18.0 | 50.0 | 2.6 | 3.939 |

TABLE 3-continued

Amino acid composition of the medium of the prior art (concentration: mg/l), part 2

| | Chemically defined medium | | | | | | |
|---|---|---|---|---|---|---|---|
| Amino acid | Trowell's T8 | Ham's F-10 | Ham's F-12 | Leibovitz's L-15 | NCTC 135 | Williams' E | Kane and Foote | MCDB 104 |
| Leu: leucine | 26.0 | 13.1 | 13.1 | 125.0 | 20.4 | 75.5 | 13.0 | 13.12 |
| Pro: proline | — | 11.5 | 34.5 | — | 6.1 | 30.0 | 11.5 | 34.53 |
| Gly: glycine | — | 7.5 | 7.5 | 200.0 | 13.5 | 50.0 | 7.5 | 7.507 |
| Ala: alanine | — | 8.9 | 8.9 | 225.0 | 31.5 | 90.0 | 8.9 | 8.909 |
| Cys: Cystein | 47.0 | 35.1 | 35.1 | 120.0* | 259.9 | 58.0 | 31.5 | 8.78 |
| Tyr: tyrosine | 18.0 | 1.8 | 5.4 | 300.0 | 16.4 | 35.0 | 1.8 | 5.436 |
| His: histidine | 10.0 | 21.0 | 21.0 | 250.0* | 26.7 | 20.3 | 23.0 | 20.97 |
| Arg: arginine | 21.0 | 210.7 | 210.7 | 500.0* | 31.2 | 60.5 | 211.0 | 210.70 |
| Tau: taurine | — | — | — | — | 4.2 | — | — | — |
| Asp: aspartic acid | — | 13.3 | 13.3 | — | 9.9 | 30.0 | 13.3 | 13.31 |
| Ser: serine | — | 10.5 | 10.5 | 200.0 | 10.8 | 10.0 | 10.5 | 10.51 |
| Asn: asparagine | — | 15.0 | 15.0 | 250.0 | 8.0 | 20.0 | 15.0 | 15.10 |
| Glu: glutamic acid | — | 14.7 | 14.7 | — | 8.3 | 50.0 | 14.7 | 14.71 |
| Gln: glutamine | — | 146.2 | 146.2 | 300.0 | 136.0 | 292.3 | 146.2 | 365.3 |
| Cys-Cys: cystine | — | — | — | — | 10.5 | 20.0 | — | — |
| Orn: ornithine | — | — | — | — | 7.4 | — | — | — |
| Amino butyric acid | — | — | — | — | 5.5 | — | — | — |
| Hydroxy proline | — | — | — | — | 4.1 | — | — | — |

In Tables 2 and 3, the symbols a), b) and c) are the same as those in Table 1, and the symbol * means amino acid as a free base.

DETAILED DESCRIPTION OF INVENTION

The medium composition of the present invention preferably contains twenty-one amino acids in the concentrations (mg/l) shown in the following Table 4:

TABLE 4

| L-phenylalanine | 0.69–13.8 |
| L-tryptophan | 0.67–13.5 |
| L-lysine | 2.44–48.8 |
| L-threonine | 1.48–29.5 |
| L-valine | 1.66–33.1 |
| L-methionine | 0.21–4.3 |
| L-isoleucine | 0.45–9.0 |
| L-leucine | 0.79–15.8 |
| L-proline | 1.17–23.4 |
| glycine | 1.16–23.2 |
| L-alanine | 2.66–53.2 |
| L-tyrosine | 0.77–15.4 |
| L-histidine | 1.63–32.5 |
| L-arginine | 1.12–1,000 |
| L-taurine | 0.39–7.8 |
| L-aspartic acid | 0.09–1.71 |
| L-serine | 0.78–15.5 |
| L-asparagine | 0.97–19.5 |
| L-glutamic acid | 1.36–27.2 |

TABLE 4-continued

| L-glutamine | 2.61–1,000 |
| L-cystine | 0.14–2.7 |

In Table 4, the upper limit for each of amino acids (for example, 13.8 for L-phenylalanine) is calculated by (mean of Table 1 (F group))×about 2, and the lower limit (for example, 0.69 for L-phenylalanine) is also calculated by (mean of Table 1 (F group))×about 0.1. However, the upper limits of L-arginine and glutamine are 1,000. Any media containing the amino acids in the concentration ranges of Table 4 are understood to be useful as medium compositions for in vitro fertilization as shown by the working examples and test examples.

As described above, the medium composition for in vitro fertilization of the present invention is characterized by the actual selection of the composition of twenty-one amino acids, in addition, in that the concentrations of amino acids are relatively lower, compared with those of the conventional medium compositions used so far for in vitro fertilization, in particular, it is noted that the contents of methionine, leucine, L-aspartic acid and cystine are lower.

The amino acids essential in the medium composition of the present invention may be used, not only in the free form, but also in the salt-forms to be pharmacologically acceptable (for example, metallic salts such as sodium salts, potassium salts and the like, mineral acid salts such as hydrochloride salts, sulfate salts and the like, organic acid salts such as acetate, lactate and the like, or hydrate). Any substances which can be converted to free amino acid by hydrolysis, for example, esters, N-acyls such as N-lower alkanoyls, oligopeptides such as di or tripeptide and the like may be used. All or one part of the L-cystine may be replaced by L-cysteine.

In the medium for in vitro fertilization of the present invention, in addition to the twenty-one amino acids as described above, sugars, electrolytes, vitamins, trace metal elements, hormones, cell growth factors, lipids or their structural components, carrier proteins, extracellular substrate components (adhesive factors), reducing substances and the like may be formulated, if necessary.

The sugars are exemplified by glucose, maltose, fructose, xylitol, sorbitol, trehalose etc. The electrolytes are exemplified by sodium chloride, sodium acetate, sodium citrate, potassium chloride, calcium chloride, calcium gluconate, magnesium chloride, magnesium sulfate, potassium dihydrogenphosphate, sodium bicarbonate, sodium pyruvate, sodium lactate and the like. The vitamins are exemplified by vitamin A, the B vitamins, vitamin C, the D vitamins, vitamin E, nicotinic acid, biotin, folic acid and the like. The rare metal elements are exemplified by zinc, iron, manganese, copper, iodine, selenium, cobalt and the like.

The hormones include insulin, hydrocortisone, dexamethasone, triiodothyronine and the like. The cell growth factors include epithelial cell growth factors, fibroblastic growth factors, platelet-derived growth factors, insulin-like growth factors, growth hormones and the like. The lipids or their structural components include essential unsaturated fatty acids such as oleic acid, linoleic acid, linolenic acid, cholesterol, ethanolamine, choline and the like. The carrier proteins include serum albumins, transferring and the like. The extracellular substrate components (adhesive factors) include fibronectins, collagen, gelatine and the like. The reducing substances include 2-mercaptoethanol, dithiothreitol, reducing type glutathione and the like.

In the medium composition of the present invention, for example, antibiotics such as penicillin, streptomycin, kanamycin, gentamicin, erythromycin etc., and antimycotic agents such as amphotericin B, nystatin etc. may be suitably added.

Further, the medium of the present invention can be used together with the known balanced salt solutions (BSS) or culture media by mixing. The equilibrium salt solutions include Tyrode's solution, Klebs-Ringer bicarbonate solution, Earle's BSS, Hanks' BSS, Dulbecco phosphoric acid buffer solution or their modified solutions. The culture media include 199 medium, BME medium, CMRL 1066 medium, MEM medium, McCoy's 5A medium, Waymouth's medium, Trowell's T-8 medium, Ham's medium, Leibovitz's L-15 medium, NCTC medium, William's E medium, Kane and Foote medium, MCDB 104 medium, Brinster medium, m-Tyrode's BSS, BWW medium, Whitten medium, TYH medium, Hoppes & Pitts medium, m-KRB medium, BO medium, T6 medium, HTF medium, GPM medium and their modified media.

The medium composition of the present invention can be prepared by formulating the components using a conventional method, and may be used in the form of a liquid product, or if necessary, in the form of a solid or semi-solid. Preferably, the medium of the present invention is prepared and provided using a conventional method in the form of a sterile solution, a sterile concentrated solution to be diluted for use or a sterile freeze-drying mixture to be thawed for use. When it is prepared, using the conventional method, harmless, pharmaceutically acceptable additives such as pH regulators, stabilizers, expanders and the like may be applied, if necessary. The pH regulators include hydrochloric acid, acetic acid, sodium hydroxide and the like, and the stabilizers include HEPES (N-2-hydroxy ethyl piperidine-N'-2-ethane sulfonic acid), sodium sulfite, sodium hydrogen sulfite, sodium pyrosulfite. Also, pH indicators such as phenol red may be added.

In order to prevent changes in the formulation composition due to interaction between the sugars, particularly the reducing sugars and the amino acids or between the calcium or magnesium salt compounds and the hydrocarbonate salt compounds, a part of the formulation components may be provided in the form of kit in which a part of the formulation components is separated and filled into another vessel or vessels. For example, a combination preparation comprises three preparations: (1) the amino acids, (2) the electrolytes except sodium bicarbonate and sugars, and (3) the sodium bicarbonate, or two preparations: (1) the amino acids, the electrolytes except for sodium bicarbonate and sugars and (2) the sodium bicarbonate.

The medium composition of the present invention can be applied to the culture of eggs or early embryos or the preparation or culture of sperm in all mammalia, in particular, it is suitable for the culture of early human embryos and effective for the stimulation of growth and qualitative stabilization of early embryos

EXAMPLE

The following examples serve to illustrate the present invention without, however, limiting the same thereto.

Example 1

A medium having the composition components shown in the following Table 5 was prepared as follows. The concentration of amino acids used corresponds to the value of the F group (the mean value of the amounts determined in the follicular fluid).

Firstly, among the composition components, the amino acids was dissolved into water for injection at fixed concentrations, followed by filtration and sterilization using a membrane filter having pore size of 0.22 micro meters (manufactured by Millipore, Mylex GV). This solution was poured into a 100 ml glass vial under sterile conditions and then freeze-dried by a conventional method (manufactured by Kyowa, RLS-301 BS) to give Preparation (1) of the amino acids. Also, among the components of the following Table 5, the electrolytes other than sodium bicarbonate and sugars were dissolved and diluted using water for injection, poured into a 100 ml glass vial under sterile conditions and then sterilized by heating using the conventional method after sealing to give Preparation (2) of electrolytes/sugars. Further, sodium bicarbonate was dissolved and diluted using water for injection, poured into a 100 ml glass vial under sterile conditions, and then sterilized by heating using a conventional method after replacing any air in the space with nitrogen and sealing to give Preparation (3) of sodium bicarbonate. Preparation (1) of amino acids, Preparation (2) of electrolytes/sugars, and Preparation (3) of sodium bicarbonate were mixed under sterile conditions to give the concentrations given in Table 5, and 0.5% (final concentration) of calf serum albumin (manufactured by Sigma) was added thereto to give the desired medium for in vitro fertilization.

TABLE 5

| component | composition range |
|---|---|
| L-phenylalanine | 6.89 mg/l |
| L-tryptophan | 6.74 mg/l |
| L-lysine hydrochloride | 24.42 mg/l |
| L-threonine | 14.77 mg/l |
| L-valine | 16.56 mg/l |
| L-methionine | 2.13 mg/l |
| L-isoleucine | 4.48 mg/l |
| L-leucine | 7.88 mg/l |
| L-proline | 11.68 mg/l |
| glycine | 11.59 mg/l |
| L-alanine | 26.62 mg/l |
| L-tyrosine | 7.70 mg/l |
| L-histidine hydrochloride (monohydrate) | 16.25 mg/l |
| L-arginine hydrochloride | 11.22 mg/l |
| L-taurine | 3.92 mg/l |
| L-aspartic acid | 0.86 mg/l |
| L-serine | 7.76 mg/l |
| L-asparagine (monohydrate) | 9.73 mg/l |
| L-glutamic acid | 13.62 mg/l |
| L-glutamine | 26.13 mg/l |
| L-cystine | 1.35 mg/l |
| sodium chloride | 5.938 mg/l |
| potassium chloride | 0.350 mg/l |
| calcium chloride (dihydrate) | 0.300 mg/l |
| magnesium sulfate (heptahydrate) | 0.049 mg/l |
| sodium bicarbonate | 2.100 mg/l |
| potassium hydrogenphosphate | 0.050 mg/l |
| sodium pyruvate | 0.036 mg/l |
| sodium lactate | 2.398 mg/l |
| glucose | 0.500 mg/l |

Example 2

Formulation was carried out in the same manner as in Example 1 except that the amino acids in the components were employed at the concentration in the following Table 6. The concentration of the amino acids used corresponds to the value of the S group (the mean value of the amounts determined in the serum).

TABLE 6

| component | composition range (mg/l) |
|---|---|
| L-phenylalanine | 9.27 |
| L-tryptophan | 7.78 |
| L-lysine hydrochloride | 30.04 |
| L-threonine | 16.93 |
| L-valine | 21.86 |
| L-methionine | 3.13 |
| L-isoleucine | 7.63 |
| L-leucine | 14.15 |
| L-proline | 12.55 |
| glycine | 13.66 |
| L-alanine | 28.29 |
| L-tyrosine | 8.69 |
| L-histidine hydrochloride (monohydrate) | 18.89 |
| L-arginine hydrochloride | 15.93 |
| L-taurine | 15.48 |
| L-aspartic acid | 2.87 |
| L-serine | 13.31 |
| L-asparagine (mono hydrate) | 11.60 |
| L-glutamic acid | 13.20 |
| L-glutamine | 29.29 |
| L-cystine | 1.44 |

Example 3

Formulation was conducted as in Example 1 except that the amino acids in the components were employed at the concentrations in the following Table 7. The concentration of the amino acids used is calculated by (the value of the F group (the mean value of the amounts determined in the serum))×0.1. Hereinafter, media containing such concentrations of amino acids are referred to as the "F 0.1 group".

TABLE 7

| component | composition range (mg/l) |
|---|---|
| L-phenylalanine | 0.689 |
| L-tryptophan | 0.674 |
| L-lysine hydrochloride | 2.442 |
| L-threonine | 1.477 |
| L-valine | 1.656 |
| L-methionine | 0.213 |
| L-isoleucine | 0.448 |
| L-leucine | 0.778 |
| L-proline | 1.168 |
| glycine | 1.159 |
| L-alanine | 2.662 |
| L-tyrosine | 0.770 |
| L-histidine hydrochloride (monohydrate) | 1.625 |
| L-arginine hydrochloride | 1.122 |
| L-taurine | 0.392 |
| L-aspartic acid | 0.086 |
| L-serine | 0.776 |
| L-asparagine (monohydrate) | 0.973 |
| L-glutamic acid | 1.362 |
| L-glutamine | 2.613 |
| L-cystine | 0.135 |

Example 4

Formulation was conducted as in Example 1 except that the amino acids in the components were used at the concentrations in the following Table 8. The concentration of the amino acids used is calculated by (the value of F group (the mean value of the amounts determined in the serum))× 2. Hereinafter, media containing such concentrations of amino acids are referred to as the "F 2 group".

TABLE 8

| component | composition range (mg/l) |
|---|---|
| L-phenylalanine | 13.78 |
| L-tryptophan | 13.48 |
| L-lysine hydrochloride | 48.83 |
| L-threonine | 29.54 |
| L-valine | 33.13 |
| L-methionine | 4.26 |
| L-isoleucine | 8.96 |
| L-leucine | 15.77 |
| L-proline | 23.35 |
| glycine | 23.17 |
| L-alanine | 53.23 |
| L-tyrosine | 15.39 |
| L-histidine hydrochloride (monohydrate) | 32.50 |
| L-arginine hydrochloride | 22.43 |
| L-taurine | 7.84 |
| L-aspartic acid | 1.71 |
| L-serine | 15.51 |
| L-asparagine (mono hydrate) | 19.46 |
| L-glutamic acid | 27.24 |
| L-glutamine | 52.27 |
| L-cystine | 2.70 |

Example 5

Formulation was conducted as in Example 1 except the use of 1000 mg/l of glutamine.

Example 6

Formulation was conducted as in Example 1 except the use of 1000 mg/l of arginine.

Example 7

Formulation was conducted as in Example 1 except the use of 1000 mg/l of glutamine and arginine.

Example 8

Formulation was conducted as in Example 1 except that the electrolytes and sugars were used at the concentrations given in the following Table 9.

TABLE 9

| component | composition range (g/l) |
| --- | --- |
| sodium chloride | 6.800 |
| potassium chloride | 0.400 |
| calcium chloride | 0.200 |
| magnesium sulfate (heptahydrate) | 0.200 |
| sodium bicarbonate | 2.000 |
| sodium dihydrogenphosphate (monohydrate) | 0.140 |
| sodium pyruvate | 0.036 |
| sodium lactate | 2.398 |
| glucose | 0.500 |

Example 9

Formulation was conducted as in Example 1 except replacing the composition and concentration of the electrolytes and sugars by those of the following Table 10.

TABLE 10

| component | composition range (g/l) |
| --- | --- |
| sodium chloride | 7.400 |
| potassium chloride | 0.285 |
| calcium chloride | 0.033 |
| magnesium sulfate | 0.075 |
| sodium bicarbonate | 1.200 |
| disodium hydrogenphosphate | 0.156 |
| potassium dihydrogenphosphate | 0.083 |
| sodium pyruvate | 0.036 |
| sodium lactate | 2.398 |
| glucose | 0.500 |

Example 10

Formulation was conducted as in Example 1 except that the types and concentrations of the electrolytes and sugars were replaced with those in the following Table 11.

TABLE 11

| component | composition range (g/l) |
| --- | --- |
| sodium chloride | 5.540 |
| potassium chloride | 0.356 |
| calcium lactate (pentahydrate) | 0.527 |
| magnesium sulfate | 0.294 |

TABLE 11-continued

| component | composition range (g/l) |
| --- | --- |
| sodium bicarbonate | 2.106 |
| potassium dihydrogenphosphate | 0.162 |
| sodium pyruvate | 0.036 |
| sodium lactate | 2.398 |
| glucose | 0.500 |

Test Example 1

(1) Collecting Embryos in Pronucleus Phase of Mouse

To ICR female mice (Nippon SLC, Nippon Clea), five international units of PMSG (pregnant mare serum gonadotrophin, Teikokuzoki Seiyaku, Serotropin (trade name)) was intraperitoneally administered, and then after 48 hours, five international units of hCG (human chorionic gonadotrophin, Teikokuzoki Seiyaku, Gonatropin (trade name) 1000) was intraperitoneally administered, thereby, inducing excess-ovulation in the mice. Subsequently, the female mice were stayed to mate overnight together with the same species of male mice, and on the next morning, from the female mice showing vagina plug, their embryos in a pronucleus phase were collected into droplets of HTF medium containing 0.5% of calf serum albumin (a medium in which the amino acids in the medium of Example 1 were excluded).

After granulosa cells were removed by treatment with 0.1% of hyaluronidase, embryos in a pronucleus phase were removed into droplets of fresh HTF medium containing 0.5% of calf serum albumin and washed to remove any degenerated ova. The resulted embryos were immediately utilized as specimens in the following experiment.

(2) Effect of Medium of Example 1 or 2 on the Growth of Embryos of a Mouse

One hundred micro litters of spots of the medium obtained in Example 1 (F group), the medium obtained in Example 2 (S group) and, as a control, HTF medium (C group) were formed under mineral oil on culture dishes (manufactured by Corning) of 60 mm in diameter, and allowed to stand for overnight under a carbon dioxide gas atmosphere under a carbon dioxide culture incubator (manufactured by Tabai, BNA-120D) for pre-equilibrium, and followed by shifting 6–29 of the embryos collected in the above test thereto and incubation under an atmosphere of 5% of $CO_2$ at 37++++. On the 1st, 3rd, 4th, 5th and 6th days after incubation, the growth of the embryos was observed by an invert microscope (manufactured by Nikon, DIAPHOT-TMD) with 100 times magnification, and, during the growth stages from the two cells phase to the disengaged embryos phase, the embryos attained to each of the stages were counted. The results obtained are listed in Table 12.

TABLE 12

| test group | times of test | counts of used embryos | growth stage | | | |
|---|---|---|---|---|---|---|
| | | | 2-cells | morulae | blasto-cysts | hatching blasto-cysts |
| C | 5 | 83 | 61(74%) | 27(33%) | 18(22%) | 7(8%) |
| F | 5 | 85 | 71(84%) | 59(69%)** | 41(58%)** | 32(38%)** |
| S | 5 | 81 | 73(90%) | 49(61%)** | 31(38%)* | 24(30%)** |

C: C group, HTF medium
F: F group, Example 1
S: S group, Example 2
*The significant difference is evaluated at 5% of level of significance, compared with C group (control, HTF medium).
**The significant difference is evaluated at 1% of level of significance, compared with C group (control, HTF medium).

Table 12 shows that the growth of embryos after the 2 cells phase in the C group (HTF medium) was significantly suppressed, while, in any group incubated in the medium having the amino acids composition of the present invention, the growth of embryos after the morula phase were evidently increased, with the effectiveness on the growth stimulation of embryos being proved.

Test Example 2
Effect of Medium of Example 3 or 4 on Growth of Embryos

The medium obtained in Example 3 (F0.1 group) and the medium obtained in Example 4 (F2 group) as well as HTF medium as a control were treated in a similar manner to Test Example 1, and the growth of embryos was observed. The results are shown in Table 13.

TABLE 13

| test group | times of test | counts of used embryos | growth stage | | | |
|---|---|---|---|---|---|---|
| | | | 2-cells | morulae | blasto-cysts | hatching blasto-cysts |
| C | 6 | 95 | 79(83%) | 46(48%) | 36(38%) | 26(27%) |
| F0.1 | 6 | 96 | 82(85%) | 64(67%)* | 48(50%) | 44(46%)** |
| F | 6 | 90 | 76(84%) | 70(78%)** | 57(63%)** | 52(58%)** |
| F2 | 6 | 89 | 75(84%) | 57(64%)* | 42(47%)+ | 34(38%)++ |

C: C group, HTF medium
F0.1: F0.1 group, Example 3
F: F group, Example 1
F2: F2 group, Example 4
*The significant difference is evaluated at 5% of level of significance, compared with C group (control, HTF medium).
**The significant difference is evaluated at 1% of level of significance, compared with C group (control, HTF medium).
+ The significant difference is evaluated at 5% of level of significance, compared with F group (Example 1).
++ The significant difference is evaluated at 1% of level of significance, compared with F group (Example 1).

As shown in Table 13, the growth in the media having the amino acid-composition according to the present invention evidently increased as described in Test Example 1, with the effectiveness on the growth stimulation of embryos being proved.

Test Example 3
Comparison Test Between the Medium of Example 1 and the Conventional Media As controls, HTF medium alone (C group), HTF medium to which amino acids of the same composition as Ham F-10 medium had been added (Ham group), HTF medium to which amino acids of the same composition as MEM medium had been added, and HTF medium to which amino acids of the same composition as Dulbecco's MEM medium had been added were used, treated in a similar manner to Test Example 1 and compared with the medium obtained in Example 1 (F group), relating to the growth of embryos. The results are shown in Table 14.

TABLE 14

| test group | times of test | counts of used embryos | growth stage | | | |
|---|---|---|---|---|---|---|
| | | | 2-cells | morulae | blasto-cysts | hatching blasto-cysts |
| C | 6 | 103 | 90(87%) | 43(42%) | 34(33%) | 26(25%) |
| F | 6 | 101 | 86(85%) | 74(73%)** | 65(64%)** | 54(54%)** |
| Ham | 6 | 97 | 85(88%) | 56(58%)**,++ | 47(49%)*,+ | 43(44%)** |
| MEM | 6 | 97 | 77(79%) | 38(39%)+ | 22(23%)++ | 13(13%)*,++ |
| DMEM | 6 | 93 | 80(86%) | 60(65%)** | 32(34%)++ | 24(26%)++ |

C: C group, HTF medium
F: F group, Example 1
Ham: Ham group, HTF + Ham's
MEM: MEM group, HTF + MEM
DMEM DMEM group, HTF + Dulbecco's
*The significant difference is evaluated at 5% of level of significance, compared with C group (control, HTF medium).
**The significant difference is evaluated at 1% of level of significance, compared with C group (control, HTF medium).
+ The significant difference is evaluated at 5% of level of significance, compared with F group (Example 1).
++ The significant difference is evaluated at 1% of level of significance, compared with F group (Example 1).

Table 14 shows that the medium group containing the amino acid composition of the present invention was good or tended to have good properties relating to the growth of embryos after the morula phase, when compared with any of the control groups.

Test Example 4
Effect of High Content-glutamine and Arginine on the Growth of Embryos In order to examine the effect of glutamine and arginine on the growth of embryos, the medium containing a high content of glutamine obtained in Example 5 (F-Gln group), the medium containing a high content of arginine obtained in Example 6 (F-Arg group), the medium containing high contents of glutamine and arginine obtained in Example 7 (F-Gln/Arg group) and the medium obtained in Example 1 (F group) as well as HTF medium (C group) were treated in a similar manner to Example 1, and the growth of embryos was observed. The results are shown in Table 15.

TABLE 15

| test group | times of test | counts of used embryos | growth stage | | | |
|---|---|---|---|---|---|---|
| | | | 2-cells | morulae | blasto-cysts | hatching blasto-cysts |
| C | 2 | 41 | 29(71%) | 14(34%) | 9(22%) | 4(10%) |
| F | 2 | 43 | 34(79%) | 28(65%)** | 17(40%) | 15(35%)** |
| F-Gln | 2 | 39 | 32(82%) | 27(69%)** | 18(46%)* | 16(41%)** |
| F-Arg | 2 | 40 | 34(85%) | 32(80%)** | 28(70%)**,++ | 23(58%)**,+ |
| F-Gln/Arg | 2 | 39 | 31(80%) | 27(69%)** | 20(51%)** | 17(44%)** |

C: C group, HTF medium
F: F group, Example 1
F-Gln: F-Gln group, high content of glutamine
F-Arg: F-Arg group, high content of arginine
F-Gln/Arg: F-Gln/Arg group
*The significant difference is evaluated at 5% of level of significance, compared with C group (control, HTF medium).
**The significant difference is evaluated at 1% of level of significance, compared with C group (control, HTF medium).
+ The significant difference is evaluated at 5% of level of significance, compared with F group (Example 1).
++ The significant difference is evaluated at 1% of level of significance, compared with F group (Example 1).

Table 15 clearly shows that the media to which a high content of glutamine and/or arginine have been added substantially stimulated the growth of embryos or tended to stimulate the growth, when compared with the control group.

Test Example 5
Effect of Essential Amino Acids and Non-essential Acids on the Growth of Embryos Two media (FE group and FNE group) in which non-essential amino acids and essential amino acids had been excluded, respectively, from the medium obtained in Example 1 (F group) were prepared in a similar manner to Example 1. These media and the above C group as a control were treated as described in Test Example 1, and the growth of embryos was observed. The results are shown in Table 16.

TABLE 16

| | | | growth stage | | | |
|---|---|---|---|---|---|---|
| test group | times of test | counts of used embryos | 2-cells | morulae | blasto-cysts | hatching blasto-cysts |
| C | 4 | 69 | 56(81%) | 28(41%) | 18(26%) | 10(15%) |
| F | 4 | 66 | 62(94%) | 44(67%)** | 27(41%) | 25(38%)** |
| FE | 4 | 64 | 58(91%) | 19(30%)++ | 11(17%)++ | 7(11%)++ |
| FNE | 4 | 64 | 59(92%) | 42(66%)** | 21(33%) | 12(19%)+ |

C: C group, HTF medium
F: F group, Example 1
FE: FE group
FNE: FNE group
*The significant difference is evaluated at 5% of level of significance, compared with C group (control, HTF medim).
**The significant difference is evaluated at 1% of level of significance, compared with C group (control, HTF medium).
+ The significant difference is evaluated at 5% of level of significance, compared with F group (Example 1).
++ The significant difference is evaluated at 1% of level of significance, compared with F group (Example 1).

Table 16 clearly shows that, in the FE group, its embryo growth after the morula phase was substantially more suppressed than in the F group. On the other hand, in the FNE group, its growth up to the blastocyst phase was not different from the growth of the F group, but the shifting to the hatching blastocyst phase of the later growth phase was substantially suppressed. These findings suggests the essential amino acids play an important role in growth stimulation in the early growth phase while all the amino acids are responsible for a growth-stimulation in the later growth phase.

Test Example 6
Influence of Electrolytes on the Embryo Growth

In order to examine the influence of electrolytes on the embryo growth, the medium obtained in Example 1 (F group) as well as the media obtained in Examples 8–10 were treated in a similar manner to Example 1, and the growth of embryos was observed. The results are shown in Table 17.

TABLE 17

| | | | growth stage | | | |
|---|---|---|---|---|---|---|
| test group | times of test | counts of used embryos | 2-cells | morulae | blasto-cysts | hatching blasto-cysts |
| F | 1 | 27 | 27(100%) | 20(74%) | 12(44%) | 12(44%) |
| Ex. 8 | 1 | 26 | 20(77%) | 19(73%) | 13(50%) | 13(50%) |
| Ex. 9 | 4 | 26 | 24(92%) | 16(62%) | 9(35%) | 7(27%) |
| Ex. 10 | 1 | 27 | 22(81%) | 16(59%) | 11(41%) | 11(41%) |

F: F group, Example 1
Ex. 8: Example 8
Ex. 9: Example 9
Ex. 10: Example 10

Table 17 clearly shows that there were no differences between the F group and the Examples 8, 9 and 10, respectively.

EFFECT OF INVENTION

The medium of the present invention comprises a composition containing, as the essential components, twenty-one amino acids, it can be applied to the culture of mammalian ova or early embryos or to the preparation or culture of sperm, in particular, it is effective for the culture of early embryos, and it can provide excellent technical effects in which improvements in growth stimulation and qualitative stabilization of early embryos were accomplished.

What is claimed is:

1. A method of in vitro fertilization which comprises cultivating ova or preimplantation embryos in a medium prepared by formulating the components, which comprises the following amino acids in their free form or their pharmaceutically acceptable salt or ester form, the ester form being hydrolyzable to give a free form, but not any other amino acid:

L-phenylalanine, L-tryptophan, L-lysine, L-threonine, L-valine, L-methionine, L-isoleucine, L-leucine, L-proline, glycine, L-alanine, L-tyrosine, L-histidine, L-arginine, L-taurine, L-aspartic acid, L-serine, L-asparagine, L-glutamic acid, L-glutamine and L-cystine, provided that at least a part of the L-cystine may be replaced by L-cysteine, wherein the amino acids have the following concentrations (mg/l):

| | |
|---|---|
| L-phenylalanine | 0.69–13.8 |
| L-tryptophan | 0.67–13.5 |
| L-lysine | 2.44–48.8 |
| L-threonine | 1.48–29.5 |
| L-valine | 1.66–33.1 |
| L-methionine | 0.21–4.3 |
| L-isoleucine | 0.45–9.0 |
| L-leucine | 0.79–15.8 |
| L-proline | 1.17–23.4 |
| glycine | 1.16–23.2 |
| L-alanine | 2.66–53.2 |
| L-tyrosine | 0.77–15.4 |
| L-histidine | 1.63–32.5 |
| L-arginine | 1.12–1,000 |
| L-taurine | 0.39–7.8 |
| L-aspartic acid | 0.09–1.71 |
| L-serine | 0.78–15.5 |
| L-asparagine | 0.97–19.5 |
| L-glutamic acid | 1.36–27.2 |
| L-glutamine | 2.61–1,000 |
| L-cystine | 0.14–2.7. |

2. The method according to claim 1, where the medium comprises additionally at least one selected from the group consisting of sugars, electrolytes, vitamins, trace metal elements, hormones, cell growth factors, lipids or their constituents, carrier proteins, fibronectins, collagen, gelatin and reducing substances.

* * * * *